United States Patent
Alanine et al.

(10) Patent No.: US 7,348,332 B2
(45) Date of Patent: Mar. 25, 2008

(54) (3,4-DIHYDRO-QUINAZOLIN-2-YL)-INDAN-1-YL-AMINES

(75) Inventors: Alexander Alanine, Schlierbach (FR); Luca Claudio Gobbi, Overwil (CH); Sabine Kolczewski, Rheinfelden (DE); Thomas Luebbers, Loerrach (DE); Jens-Uwe Peters, Grenzach-Wyhlen (DE); Lucinda Steward, Basel (CH)

(73) Assignee: Hoffmann-La Rochse Inc., Nutley, NJ (US)

( * ) Notice: Subject to any disclaimer, the term of this patent is extended or adjusted under 35 U.S.C. 154(b) by 0 days.

(21) Appl. No.: 11/399,790

(22) Filed: Apr. 5, 2006

(65) Prior Publication Data

US 2006/0229323 A1 Oct. 12, 2006

(30) Foreign Application Priority Data

Apr. 11, 2005 (EP) ................... 05102824

(51) Int. Cl.
*A61K 31/517* (2006.01)
*C07D 239/84* (2006.01)
(52) U.S. Cl. .................... 514/266.21; 514/266.24; 514/266.4; 544/284; 544/292
(58) Field of Classification Search .......... 514/266.21, 514/266.24, 266.4; 544/284, 292
See application file for complete search history.

(56) References Cited

U.S. PATENT DOCUMENTS

| | | | |
|---|---|---|---|
| 4,379,929 A | 4/1983 | Conrad et al. | 544/292 |
| 5,444,062 A * | 8/1995 | Coe et al. | 514/266.21 |
| 5,948,775 A | 9/1999 | Koko et al. | 544/293 |

FOREIGN PATENT DOCUMENTS

| | | |
|---|---|---|
| EP | 0 087 337 | 8/1983 |
| WO | WO 92/07844 | 5/1992 |
| WO | WO 2004/096771 | 11/2004 |

OTHER PUBLICATIONS

Hoyer, et al., Pharmacol. Rev. vol. 46, pp. 157-204 (1994).
Rees et al., FEBS Letters, vol. 355, pp. 242-246 (1994).
Francken et al., Eur. J. Pharmacol. vol. 361, pp. 299-309 (1998).
Noda, et al., J. Neurochem. vol. 84, pp. 222-232 (2003).
Dubertret et al., Journal of Psychiatric Research, vol. 38, pp. 371-376 (2004).
Manetsch, et al., Chem. Eur. J., vol. 10, pp. 2487-2506 (2004).
Kosasayama, et al., Chem. Pharm. Bull. vol. 27(4), pp. 880-892 (1979).
Webb, T. et al, *Bioorganic and Medicinal Che. Ltrs*, vol. 11, 77-85 (2003) XP-002391791.

* cited by examiner

*Primary Examiner*—James O. Wilson
*Assistant Examiner*—Tamthom N Truong
(74) *Attorney, Agent, or Firm*—George W. Johnston; Patricia S. Rocha-Tramaloni; Kimberly J. Prior

(57) ABSTRACT

The present invention relates to compounds of formula

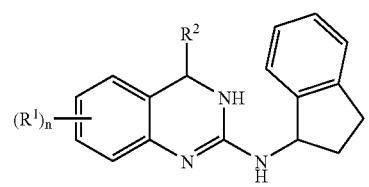

wherein
$R^1$, $R^2$, and n are as defined herein
and to pharmaceutically acceptable acid addition salts thereof.

The compounds of formula I have a good activity on the 5-$HT_{5A}$ receptor. Therefore, the invention provides the use of a compound of formula I for 5-$HT_{5A}$ receptor related diseases, such as anxiety, depression, sleep disorders and schizophrenia.

19 Claims, No Drawings

(3,4-DIHYDRO-QUINAZOLIN-2-YL)-INDAN-1-YL-AMINES

PRIORITY TO RELATED APPLICATIONS

This application claims the benefit of European Application No. 05102824.9, filed Apr. 11, 2005, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_5$A serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides compounds of formula I

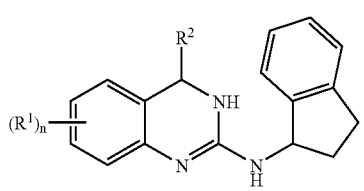

I wherein

R$^1$ is hydrogen, lower alkyl, lower alkoxy, halogen or lower alkyl substituted by halogen;

R$^2$ is hydrogen, lower alkyl, aryl or hetaryl, wherein aryl and hetaryl are each optionally substituted by one or more substituents selected from the group consisting of lower alkyl and halogen;

n is 1 or 2;

and pharmaceutically acceptable acid addition salts thereof.

The compounds of formula I can contain asymmetric carbon atoms. Accordingly, the present invention includes all stereoisomeric forms of the compounds of formula I, including each of the individual enantiomers and mixtures thereof.

The invention also provides pharmaceutical compositions that comprise a therapeutically effective amount of a compound of formula I or a pharmaceutically acceptable salt thereof and a pharmaceutically acceptable carrier.

Compounds of the invention have good activity on the 5-HT$_{5A}$ receptor. The invention also provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It must be noted that, as used herein, the singular forms "a," "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "lower alkoxy" denotes a group wherein the alkyl residues are as defined above, and which is attached via an oxygen atom.

The term "halogen" denotes chlorine, iodine, fluorine and bromine.

The term "lower alkyl substituted by halogen" denotes a lower alkyl group as defined above, wherein one or more hydrogen atom is replaced by (a) halogen atom(s), for example $CH_2F$, $CHF_2$, $CF_3$ or the like.

The term "aryl" represents a mono- or bicyclic aromatic hydrocarbon group having 6 to 10 carbon atoms, examples of such groups are phenyl or naphthyl, a preferred aryl group is phenyl.

These aryl groups are optionally further substituted by one or several substituents chosen from halogen or alkyl groups as defined above.

The term "hetaryl group" represents a 5- or 6-membered aromatic heterocyclic group having 1 or 2 heteroatoms chosen from N, O and S. Examples of such aromatic heterocyclic groups include pyridyl, pyrimidinyl, pyridazinyl, pyrrolyl, furanyl, thiophenyl, imidazolyl, pyrazolyl, isoxazolyl, isothiazolyl, thiazolyl, oxazolyl, 1,2,4-oxadiazolyl, 1,2,3-oxadiazolyl, 1,3,4-oxadiazolyl, 1,2,3-thiadiazolyl, 1,2,4-thiadiazolyl and 1,3,4-thiadiazolyl;

Preferred groups are thiophenyl and isoxazolyl.

"Thiophenyl" and "thienyl" are synonymous terms and refer to a substituent group that is a 5-membered hetaryl ring having one ring sulfur atom that is derived from thiophene.

The "hetaryl groups" are optionally further substituted by several substituents chosen from halogen or alkyl groups as defined above.

"Pharmaceutically acceptable," such as pharmaceutically acceptable carrier, excipient, etc. means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

The present invention provides compounds of formula I

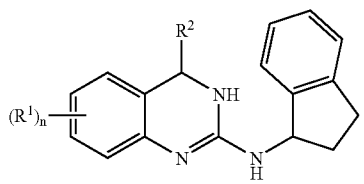

wherein
$R^1$ is hydrogen, lower alkyl, lower alkoxy, halogen or lower alkyl substituted by halogen;
$R^2$ is hydrogen, lower alkyl, aryl or hetaryl, wherein aryl and hetaryl are each optionally substituted by one or more substituents selected from the group consisting of lower alkyl and halogen;
n is 1 or 2;

and pharmaceutically acceptable acid addition salts thereof.

The compounds of formula I can contain asymmetric carbon atoms. Accordingly, the present invention includes all stereoisomeric forms of the compounds of formula I, including each of the individual enantiomers and mixtures thereof.

Preferred compounds of formula I are those, wherein $R^2$ is hydrogen, for example the following compounds:
(3,4-dihydro-quinazolin-2-yl)-(R)-indan-1-yl-amine
(5-chloro-3,4-dihydro-quinazolin-2-yl)-indan-1-yl-amine
indan-1-yl-(8-methyl-3,4-dihydro-quinazolin-2-yl)-amine
(6-fluoro-3,4-dihydro-quinazolin-2-yl)-indan-1-yl-amine
(5,6-dichloro-3,4-dihydro-quinazolin-2-yl)-indan-1-yl-amine
(5-fluoro-3,4-dihydro-quinazolin-2-yl)-indan-1-yl-amine
indan-1-yl-(6-methyl-3,4-dihydro-quinazolin-2-yl)-amine
indan-1-yl-(5-methyl-3,4-dihydro-quinazolin-2-yl)-amine
indan-1-yl-(6-methoxy-3,4-dihydro-quinazolin-2-yl)-amine
(7-chloro-3,4-dihydro-quinazolin-2-yl)-indan-1-yl-amine
indan-1-yl-(7-trifluoromethyl-3,4-dihydro-quinazolin-2-yl)-amine
indan-1-yl-(7-methoxy-3,4-dihydro-quinazolin-2-yl)-amine
(6,7-dimethoxy-3,4-dihydro-quinazolin-2-yl)-indan-1-yl-amine
(3,4-dihydro-quinazolin-2-yl)-(S)-indan-1-yl-amine and
(6-chloro-4-phenyl-3,4-dihydro-quinazolin-2-yl)-indan-1-yl-amine.

Further preferred are compounds, wherein $R^2$ is alkyl, in particular, those wherein the $R^2$ is methyl, for example the following compounds:
indan-1-yl-(4-methyl-3,4-dihydro-quinazolin-2-yl)-amine and
(6,7-dichloro-4-methyl-3,4-dihydro-quinazolin-2-yl)-indan-1-yl-amine.

Preferred are further compounds, wherein $R^2$ is aryl optionally substituted by one or more substituents selected from lower alkyl and halogen. In particular, preferred compounds are those wherein $R^2$ is phenyl, optionally substituted by halogen, for example
indan-1-yl-(4-phenyl-3,4-dihydro-quinazolin-2-yl)-amine
[4-(2,5-dichloro-phenyl)-3,4-dihydro-quinazolin-2-yl]-(S)-indan-1-yl-amine,
[4-(2,5-dichloro-phenyl)-3,4-dihydro-quinazolin-2-yl]-(R)-indan-1-yl-amine,
[6-chloro-4-(2-chloro-phenyl)-3,4-dihydro-quinazolin-2-yl]-(S)-indan-1-yl-amine and
[6-chloro-4-(2-chloro-phenyl)-3,4-dihydro-quinazolin-2-yl]-(R)-indan-1-yl-amine.

Preferred are further compounds, wherein R2 is hetaryl, optionally substituted by one or more substituents selected from lower alkyl and halogen. In particular, preferred compounds are those wherein $R^2$ is thiophenyl or isoxazolyl, optionally substituted by lower alkyl, for example
(R)-indan-1-yl-(4-thiophen-3-yl-3,4-dihydro-quinazolin-2-yl)-amine,
(S)-indan-1-yl-(4-thiophen-3-yl-3,4-dihydro-quinazolin-2-yl)-amine,
[4-(3,5-dimethyl-isoxazol-4-yl)-3,4-dihydro-quinazolin-2-yl]-(R)-indan-1-yl-amine and
[4-(3,5-dimethyl-isoxazol-4-yl)-3,4-dihydro-quinazolin-2-yl]-(S)-indan-1-yl-amine.

In another embodiment, preferred compounds of the invention are those in which $R^1$ is hydrogen. Other preferred compounds are those in which $R^1$ is lower alkyl. Still other preferred compounds are those in which $R^1$ is lower alkyl substituted by halogen.

Further preferred compounds of the invention are those in which $R^1$ is halogen. Still other preferred compounds are those in which $R^1$ is lower alkoxy.

The present compounds of formula I and their pharmaceutically acceptable salts can be prepared by methods known in the art, for example by processes described below, which process comprises reacting a compound of formula

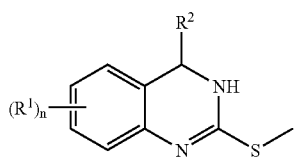

II with 1-aminoindane to obtain a compound of formula

I wherein $R^1$ and $R^2$ are as described above, and if desired, converting the compounds obtained into pharmaceutically acceptable acid addition salts.

In examples 1-26 and in the following scheme 1 the preparation of compounds of formula I is described in more detail. The starting materials are known compounds or may be prepared according to methods known in the art.

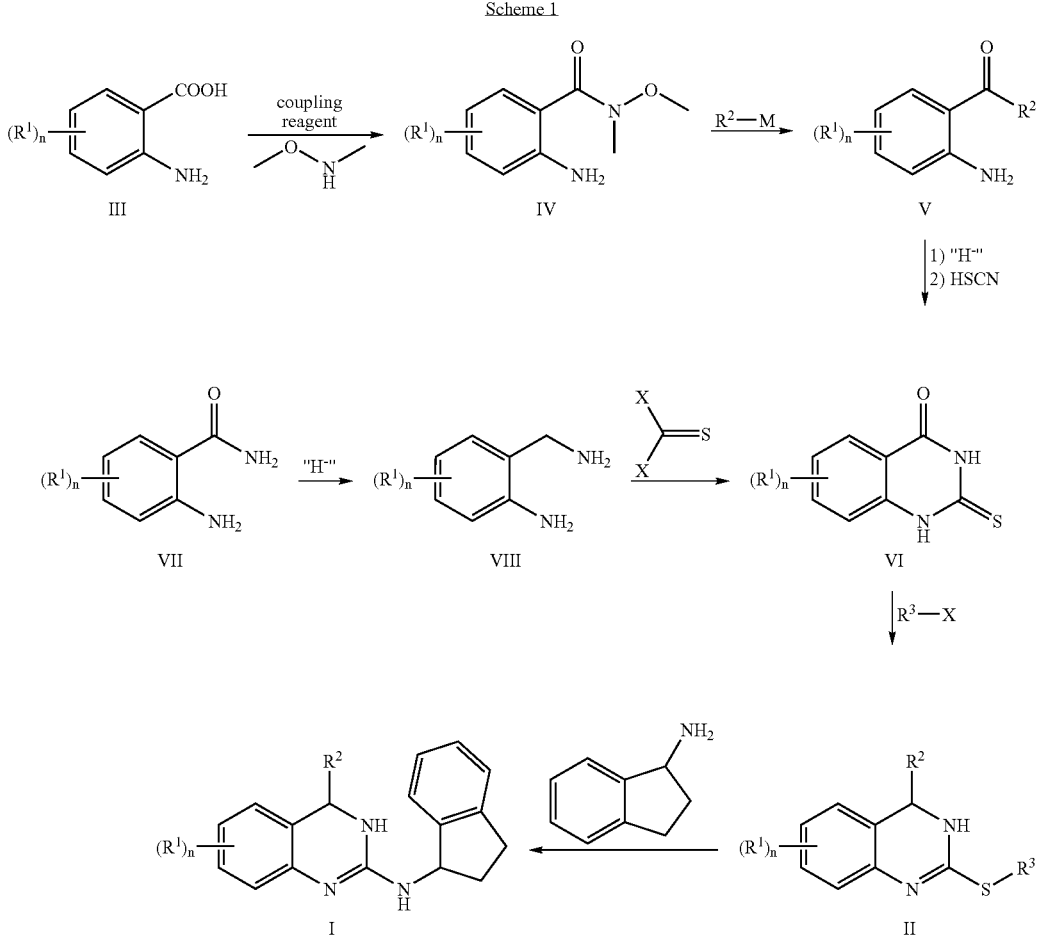

Scheme 1

$R^2$—M = metallo-organic reagent
X = leaving group
$R^3$ = lower alkyl

A 3,4-dihydro-1H-quinazoline-2-thione VI is reacted with an alkylating agent R³—X, such as methyl iodide, in a suitable solvent, such as acetone, to give a 2-alkylsulfanyl-3,4-dihydro-quinazoline II, which can be isolated from the reaction mixture by conventional methods, for instance filtration. The compound of formula II is then heated with 1-aminoindane in a suitable solvent, such as acetonitril. The corresponding (3,4-dihydro-quinazolin-2-yl)-indan-1-yl-amines of formula I can then be isolated from the reaction mixture by conventional purification.

3,4-Dihydro-1H-quinazoline-2-thiones VI can be prepared by several methods. In one such method, a 2-aminobenzamide of formula VII is reacted with a hydride transfer reagent, such as $LiAlH_4$, in a suitable solvent, such as THF. Elevated temperature might be required to carry out the reaction. After hydrolysis of excess reagent, 2-aminomethylphenylamine of formula VIII is isolated from the mixture by conventional workup and purification. The compound of formula VIII can then be reacted with thiophosgene, or a thiophosgene equivalent, in a suitable solvent, such as diethyl ether. A base, such as triethylamine, might be added to the reaction mixture to neutralize acidic by-products. After the evaporation of the solvent, the crude product can be used usually without further purification in the next step.

Another method to obtain 3,4-dihydro-1H-quinazoline-2-thiones VI is as follows: an anthranilic acid of formula III is suitably activated, for instance with a coupling reagent such as HBTU, and converted with N,O-dimethylhydroxylamine in a suitable solvent, such as DMF, and optionally in the presence of a base, such as NMM, to a Weinreb amide of formula IV. After isolation and purification by conventional means, the compound of formula IV is then converted with a metalloorganic reagent $R^2$-M, such as alkyllithium, in a suitable solvent, such as THF, for instance by allowing the reaction mixture to warm from low temperature, e.g. −78° C., to room temperature. Conventional workup and purification then gives a phenylalkanone of formula V. The compound of formula V can be converted to a 3,4-dihydro-1H-quinazoline-2-thione of formula VI in a reaction sequence that might be conducted without isolation of intermediates. In a suitable solvent, the compound of formula V is reacted first with a hydride reagent, such as sodium borohydride, and subsequently, with HSCN, which might be generated in situ from thiocyanate salt, e.g. KSCN, and an acid, e.g. HCl. Elevated temperature is usually necessary to carry out the reaction. The compound of formula VI can then be obtained by conventional workup and purification of the reaction mixture.

The following abbreviations have been used:
HBTU=O-benzotriazol-1-yl-N,N,N',N'-tetramethyluronium hexafluorophosphate
DMF=N,N-dimethylformamide
NMM=N-methylmorpholine
THF=tetrahydrofuran As mentioned earlier, the compounds of formula I and their pharmaceutically acceptable addition salts possess valuable pharmaceutical properties. Compounds of the present invention are active on the $5-HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The most preferred indications in accordance with the present invention are those, which include disorders of the nervous system, are for example, the treatment of anxiety, depression, sleep disorders and schizophrenia.

Test Description

A [³H]LSD radioligand binding assay was used to determine the affinity of the compounds for the recombinant human $5-HT_{5A}$ receptor, in membranes from transiently (cDNA) expressed $5-HT_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 µM pargyline. The binding assay was carried out in 96-well-plates in the presence of [³H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation.

The activity of the present compounds is described in the table below:

| Example | Ki (nM) |
|---------|---------|
| 1 | 25 |
| 2 | 32 |
| 3 | 32 |
| 4 | 35 |
| 5 | 39 |
| 6 | 48 |
| 7 | 50 |
| 8 | 55 |
| 9 | 80 |
| 10 | 71 |
| 11 | 125 |
| 12 | 174 |
| 13 | 260 |
| 14 | 310 |
| 15 | 310 |
| 16 | 350 |
| 17 | 350 |
| 18 | 410 |
| 19 | 550 |
| 20 | 550 |
| 21 | 595 |
| 22 | 655 |
| 23 | 133 |
| 24 | 293 |
| 25 | 863 |
| 26 | 1200 |

The present invention also provides pharmaceutical compositions containing compounds of formula I or pharmaceutically acceptable salts thereof and a pharmaceutically acceptable carrier. Such pharmaceutical compositions can be administered orally, e.g. in the form of tablets, coated tablets, dragees, hard and soft gelatin capsules, solutions, emulsions or suspensions. The administration can, however, also be effected rectally, e.g. in the form of suppositories, parenterally, e.g. in the form of injection solutions.

The pharmaceutical compositions of the invention, in addition to one or more compound of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing one or more compounds of formula I and/or pharmaceutically acceptable acid addition salts and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 1 | 0 | 15 | 10 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I can be prepared as shown in the following description:

Preparation of 2-aminobenzylamines as Starting Materials a) 2-Aminomethyl-6-methyl-phenylamine

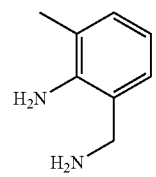

Under an atmosphere of argon, a solution 2-amino-3-methylbenzamide (1.2 g, 80 mmol) in THF (25 ml) was added to a suspension of $LiAlH_4$ (1.52 g, 40 mmol) in THF (25 ml) over 20 min. The suspension was heated to reflux (4 h). For workup, the mixture was cooled to 0° C., and 1.5 ml $H_2O$, 3 ml 4n NaOH, and 3 ml $H_2O$ were added subsequently. The suspension was dried ($Na_2SO_4$), and evaporated under reduced pressure. The title compound (338 mg, 31%) was isolated from the residue by chromatographic purification (silica gel, $CH_2Cl_2$/MeOH (2M $NH_3$)=9:1).

MS: m/e=136 [M+].

$^1$H NMR ($CDCl_3$): δ 2.20 (3H, s), 3.92 (2H, s), 6.64 (1H, t), 6.92 (1H, d), 6.99 (1H, d).

b) 2-Aminomethyl-4-methyl-phenylamine

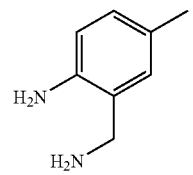

The title compound was prepared in analogy to a) (2-aminomethyl-6-methyl-phenylamine) from 2-amino-5-methyl-benzamide.

MS: m/e=136 [M+]. $^1$H NMR ($CDCl_3$): δ 2.23 (3H, s), 3.86 (2H, s), 6.61 (1H, d), 6.88 (2H, m).

c) 2-Aminomethyl-5-trifluoromethyl-phenylamine

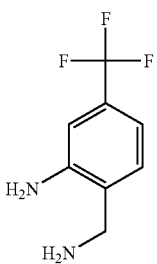

The title compound was prepared in analogy to a) (2-aminomethyl-6-methyl-phenylamine) from 2-amino-4-trifluorobenzamide. 2-Amino-4-trifluorobenzamide can be prepared by the method of Anderson, P. L., U.S. Pat. No. 4,307,113, 1981.

MS: m/e=190 [M+]. $^1$H NMR (CDCl$_3$): δ 1.45 (4H, bs), 3.94 (2H, s), 6.88 (1H, s), 6.92 (1H, d), 7.10 (1H, d).

d) 2-Aminomethyl-5-methoxy-phenylamine

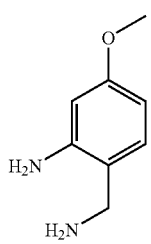

The title compound was prepared in analogy to a) (2-aminomethyl-6-methyl-phenylamine) from 2-amino-4-methoxybenzamide. 2-Amino-4-methoxybenzamide can be prepared by the method of Koko, M. C.; Santilli, A. A. U.S. Pat. No. 5,948,775, 1999.

PREPARATION OF FINAL COMPOUNDS

Example 1

(3,4-Dihydro-quinazolin-2-yl)-(R)-indan-1-yl-amine

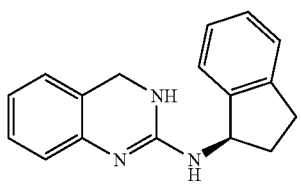

a) 2-Methylsulfanyl-3,4-dihydro-quinazoline hydroiodide

Under a atmosphere of nitrogen, a solution of thiophosgene in diethyl ether was slowly added at −78° C. to a mixture of 2-aminobenzylamine, triethylamine and diethyl ether. After being kept at −78° for an additional 15 min, the reaction mixture was allowed to warm to r.t. The precipitate was filtered, washed with diethyl ether, and dissolved in MeOH. To this solution, KOH was added, the precipitated KCl was removed by filtration, and the filtrate was evaporated under reduced pressure. The obtained product (7.55 g, 70%) was used for the next step without further purification.

Methyl iodide (11.5 ml, 184 mmol) was added to a solution of 3,4-dihydro-1H-quinazoline-2-thione (7.55 g, 46 mmol) in ethanol (150 ml), and the mixture was heated to reflux (3.5 h). The majority of the solvent was then evaporated under reduced pressure, and the precipitate was collected by filtration and washed with a small amount of cold ethanol. The thus obtained title compound (9.60 g, 68%) was used in the next step without further purification.

$^1$H NMR (d$^6$-DMSO): δ 2.74 (3H, s), 4.72 (2H, s), 7.06 (1H, d), 7.24 (2H, m), 7.35 (1H, m).

b) (3,4-Dihydro-quinazolin-2-yl)-(R)-indan-1-yl-amine

2-Methylsulfanyl-3,4-dihydro-quinazoline hydroiodide (50 mg, 0.28 mmol) and (R)-1-aminoindane (37 mg, 0.28 mmol) were suspended in acetonitrile (1 ml) and heated in a screw-capped vial to 85° C. (6 h). The product was isolated from the reaction mixture by preparative HPLC (YMC CombiPrep C18 column 50×20 mm, solvent gradient 5-95% CH$_3$CN in 0.1% TFA(aq) over 6.0 min, λ=230 nm, flow rate 40 ml/min) to give the title compound (18 mg, 24%).

MS: m/e=264.2 [M+H+]. $^1$H NMR (CDCl$_3$): δ 1.88-1.98 (1H, m), 2.55-2.61 (1H, m), 2.71-2.79 (1H, m), 2.85-2.92 (1H, m), 4.39 (2H, s), 5.12 (1H, bs), 6.94-7.26 (8H, m).

Example 2

(5-Chloro-3,4-dihydro-quinazolin-2-yl)-indan-1-yl-amine

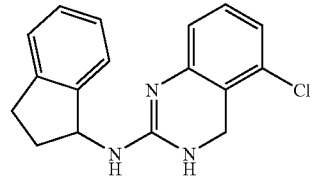

The title compound (MS: m/e=298.3 [M+H+]) was prepared in analogy to example 1 from (+/−)-1-aminoindan and 2-amino-6-chlorobenzylamine.

Example 3

Indan-1-yl-(8-methyl-3,4-dihydro-quinazolin-2-yl)-amine

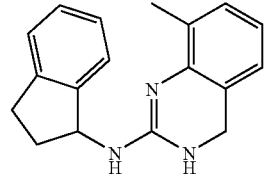

The title compound (MS: m/e=278.3 [M+H+]) was prepared in analogy to example 1 from (+/−)-1-aminoindan and 2-aminomethyl-6-methyl-phenylamine.

Example 4

(6-Fluoro-3,4-dihydro-quinazolin-2-yl)-indan-1-yl-amine

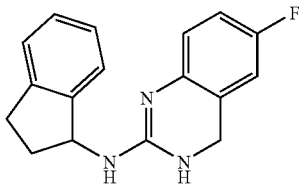

The title compound (MS: m/e=282.3 [M+H$^+$]) was prepared in analogy to example 1 from (+/−)-1-aminoindan and 2-aminomethyl-4-fluoro-phenylamine.

Example 5

(5,6-Dichloro-3,4-dihydro-quinazolin-2-yl)-indan-1-yl-amine

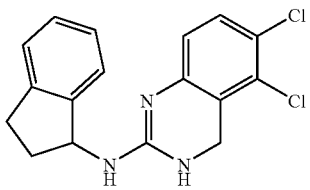

The title compound (MS: m/e=332.1 [M+H$^+$]) was prepared in analogy to example 1 from (+/−)-1-aminoindan and 2-aminomethyl-3,4-dichloro-phenylamine.

Example 6

(5-Fluoro-3,4-dihydro-quinazolin-2-yl)-indan-1-yl-amine

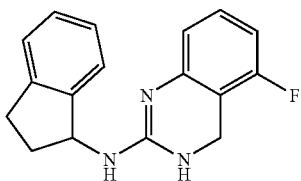

The title compound (MS: m/e=282.3 [M+H$^+$]) was prepared in analogy to example 1 from (+/−)-1-aminoindan and 2-aminomethyl-3-fluoro-phenylamine.

Example 7

Indan-1-yl-(6-methyl-3,4-dihydro-quinazolin-2-yl)-amine

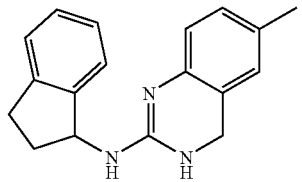

The title compound (MS: m/e=278.2 [M+H$^+$]) was prepared in analogy to example 1 from (+/−)-1-aminoindan and 2-aminomethyl-4-methyl-phenylamine.

Example 8

Indan-1-yl-(5-methyl-3,4-dihydro-quinazolin-2-yl)-amine

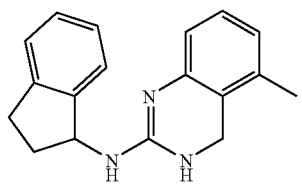

The title compound (MS: m/e=278.3 [M+H$^+$]) was prepared in analogy to example 1 from (+/−)-1-aminoindan and 2-amino-3-methylbenzylamine.

Example 9

Indan-1-yl-(4-methyl-3,4-dihydro-quinazolin-2-yl)-amine

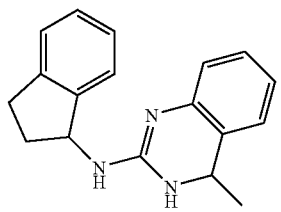

a) 4-Methyl-3,4-dihydro-1H-quinazoline-2-thione

At a temperature of 65° C., sodium borohydride (281 mg, 4.4 mmol) was added to a solution of 2-aminoacetophenone (1.00 g, 7.4 mmol) in ethanol (6 ml). The mixture was stirred overnight (65° C.). At r.t., H$_2$O (1.5 ml); a solution of potassium thiocyanate (800 mg in 1.5 ml H$_2$O, 8.2 mmol) and HCl (1.5 ml HCl conc in 2 ml H$_2$O) were added subsequently. The mixture was then stirred for 3 h at 65° C. The solvent was evaporated under reduced pressure, and the residue was taken up in ethyl acetate and washed with water. After drying (Na$_2$SO$_4$) and evaporation of the solvent, the residue was recrystallized from isopropanol to give the title compound (410 mg, 31%).

¹H NMR (d⁶-DMSO): δ 1.32 (3H, d), 4.55 (1H, q), 6.93-7.00 (2H, m), 7.12-7.19 (2H, m), 8.71 (1H, bs), 10.43 (1H, bs).

b) 4-Methyl-2-methylsulfanyl-3,4-dihydro-quinazoline hydroiodide

Methyl iodide (0.43 ml, 6.94 mmol) was added to a solution of 4-methyl-3,4-dihydro-1H-quinazoline-2-thione (410 mg, 2.30 mmol) in acetone (5 ml). The mixture was stirred for 15 min (r.t.), and the title compound (500 mg, 67%) was isolated from the reaction mixture by filtration.

¹H NMR (d⁶-DMSO): δ 1.46 (3H, d), 2.76 (3H, s), 5.02 (1H, q), 7.11 (1H, d), 7.27-7.39 (3H, m), 10.25 (1H, bs), 12.03 (1H, bs).

Indan-1-yl-(4-methyl-3,4-dihydro-quinazolin-2-yl)-amine

4-Methyl-2-methylsulfanyl-3,4-dihydro-quinazoline hydroiodide (31 mg, 0.10 mmol) and (+/−)-1-aminoindane (17 mg, 0.12 mmol) were suspended in acetonitrile (1 ml) and heated in a screw-capped vial to 85° C. (12 h). The product was isolated from the reaction mixture by preparative HPLC (YMC CombiPrep C18 column 50×20 mm, solvent gradient 5-95% CH₃CN in 0.1% TFA(aq) over 7.0 min, λ=230 nm, flow rate 40 ml/min) to give the title compound (MS: m/e=264.2 [M+H⁺]).

Example 10

(6,7-Dichloro-4-methyl-3,4-dihydro-quinazolin-2-yl)-indan-1-yl-amine

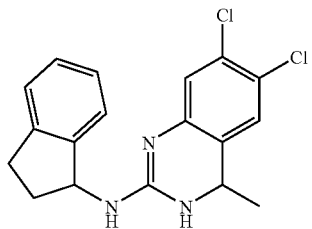

The title compound (MS: m/e=346.1 [M+H⁺]) was prepared in analogy to example 9 from 1-(2-amino-4,5-dichloro-phenyl)-ethanone. 1-(2-amino-4,5-dichloro-phenyl)-ethanone was prepared by the method of Conrad, R. A.; White, W. A. U.S. Pat. No. 4,379,929, 1983.

Example 11

Indan-1-yl-(6-methoxy-3,4-dihydro-quinazolin-2-yl)-amine

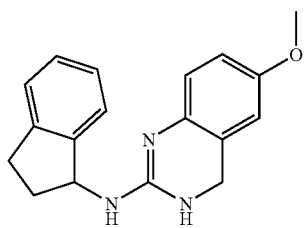

The title compound (MS: m/e=294.2 [M+H⁺]) was prepared in analogy to example 1(b) from (+/−)-1-aminoindan and 6-methoxy-3,4-dihydro-1H-quinazoline-2-thione. 6-Methoxy-3,4-dihydro-1H-quinazoline-2-thione can be prepared by the method of Manetsch, Roman; Zheng, Lei; Reymond, Martine T.; Woggon, Wolf-Dietrich; Reymond, Jean-Louis *Chemistry—A European Journal* 2004, 10(10), 2487-2506.

Example 12

(7-Chloro-3,4-dihydro-quinazolin-2-yl)-indan-1-yl-amine

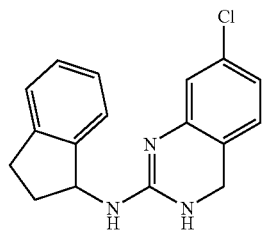

The title compound (MS: m/e=298.3 [M+H⁺]) was prepared in analogy to example 1 from (+/−)-1-aminoindan and 2-aminomethyl-5-chloro-phenylamine.

Example 13

Indan-1-yl-(7-trifluoromethyl-3,4-dihydro-quinazolin-2-yl)-amine

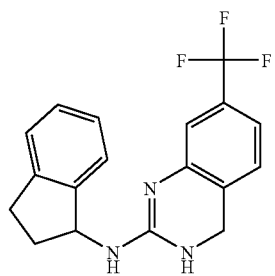

The title compound (MS: m/e=332.2 [M+H⁺]) was prepared in analogy to example 1 from (+/−)-1-aminoindan and 2-aminomethyl-5-trifluoromethyl-phenylamine.

Example 14

Indan-1-yl-(4-phenyl-3,4-dihydro-quinazolin-2-yl)-amine

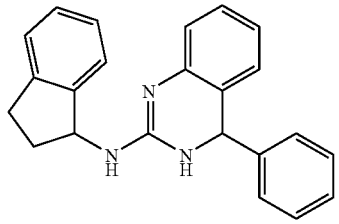

The title compound (MS: m/e=340.3 [M+H$^+$]) was prepared in analogy to example 1 (b) from (+/−)-1-aminoindan and 2-methylsulfanyl-4-phenyl-3,4-dihydro-quinazoline hydroiodide. 2-Methylsulfanyl-4-phenyl-3,4-dihydro-quinazoline hydroiodide can be prepared by the method of Kosasayama, A.; Higashi, K.; Ishikawa, F. *Chem. Pharm. Bull.* 1979, 27(4), 880-892.

Example 15

Indan-1-yl-(7-methoxy-3,4-dihydro-quinazolin-2-yl)-amine

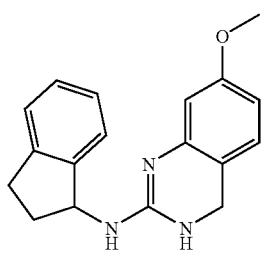

The title compound (MS: m/e=294.2 [M+H$^+$]) was prepared in analogy to example 1 from (+/−)-1-aminoindan and 2-aminomethyl-5-methoxy-phenylamine.

Example 16

(6,7-Dimethoxy-3,4-dihydro-quinazolin-2-yl)-indan-1-yl-amine

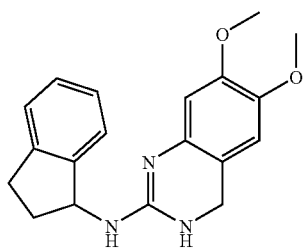

The title compound (MS: m/e=324.3 [M+H$^+$]) was prepared in analogy to example 1 from (+/−)-1-aminoindan and 2-aminomethyl-4,5-dimethoxy-phenylamine.

Example 17

(3,4-Dihydro-quinazolin-2-yl)-(S)-indan-1-yl-amine

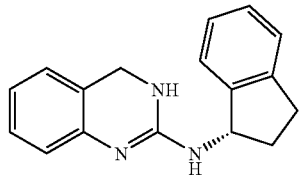

The title compound (MS: m/e=264.2 [M+H$^+$]) was prepared in analogy to example 1 from (S)-1-aminoindan and 2-aminobenzylamine.

Example 18

(6-Chloro-4-phenyl-3,4-dihydro-quinazolin-2-yl)-indan-1-yl-amine

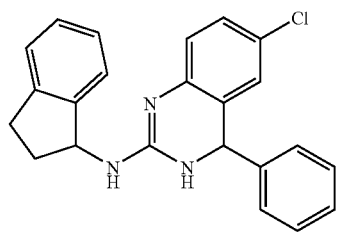

The title compound (MS: m/e=374.1 [M+H$^+$]) was prepared in analogy to example 1 (b) from (+/−)-1-aminoindan and 6-chloro-2-methylsulfanyl-4-phenyl-3,4-dihydro-quinazoline. 6-Chloro-2-methylsulfanyl-4-phenyl-3,4-dihydro-quinazoline can be prepared by the method of Richter, P.; Oertel, F. *Pharmazie* 1990, 45(10), 721-724.

Example 19

[4-(2,5-Dichloro-phenyl)-3,4-dihydro-quinazolin-2-yl]-(S)-indan-1-yl-amine

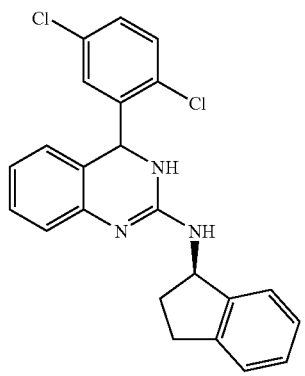

The title compound (MS: m/e=408.3 [M+H$^+$]) was prepared in analogy to example 9 from (S)-1-aminoindan and (2-amino-phenyl)-(2,5-dichloro-phenyl)-methanone.

Example 20

[4-(2,5-Dichloro-phenyl)-3,4-dihydro-quinazolin-2-yl]-(R)-indan-1-yl-amine

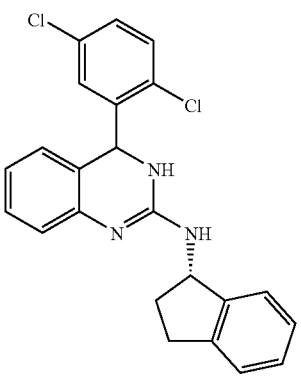

The title compound (MS: m/e=408.2 [M+H$^+$]) was prepared in analogy to example 9 from (R)-1-aminoindan and (2-amino-phenyl)-(2,5-dichloro-phenyl)-methanone.

Example 21

[6-Chloro-4-(2-chloro-phenyl)-3,4-dihydro-quinazolin-2-yl]-(S)-indan-1-yl-amine

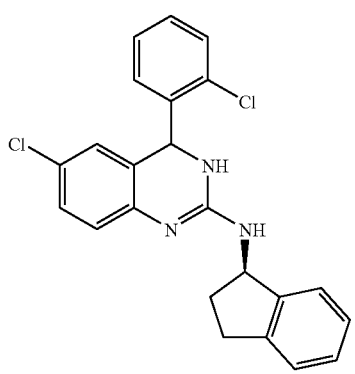

The title compound (MS: m/e=408.3 [M+H$^+$]) was prepared in analogy to example 9 from (S)-1-aminoindan and (2-amino-5-chloro-phenyl)-(2-chloro-phenyl)-methanone.

Example 22

[6-Chloro-4-(2-chloro-phenyl)-3,4-dihydro-quinazolin-2-yl]-(R)-indan-1-yl-amine

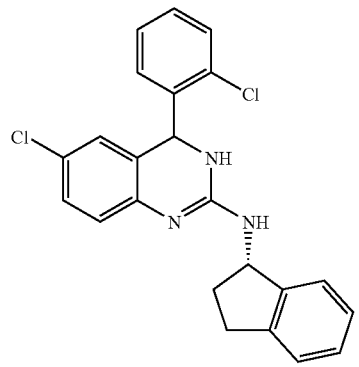

The title compound (MS: m/e=408.3 [M+H$^+$]) was prepared in analogy to example 9 from (R)-1-aminoindan and (2-amino-5-chloro-phenyl)-(2-chloro-phenyl)-methanone.

Example 23

(R)-Indan-1-yl-(4-thiophen-3-yl-3,4-dihydro-quinazolin-2-yl)-amine

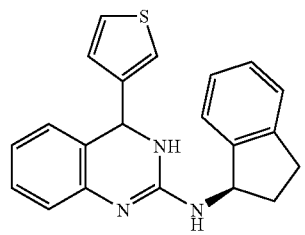

The title compound (MS: m/e=346.3 [M+H$^+$]) was prepared in analogy to example 9 from (R)-1-aminoindan and (2-amino-phenyl)-thiophen-3-yl-methanone. (2-Amino-phenyl)-thiophen-3-yl-methanone can be prepared by the method of Fritz Hunziker et. al.: *Europ. J. Med. Chem.* 1981, 16(5), 391.

Example 24

(S)-Indan-1-yl-(4-thiophen-3-yl-3,4-dihydro-quinazolin-2-yl)-amine

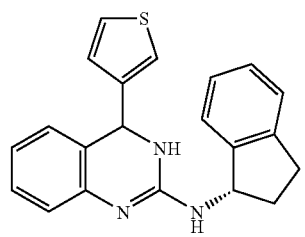

The title compound (MS: m/e=346.3 [M+H⁺]) was prepared in analogy to example 9 from (S)-1-aminoindan and (2-amino-phenyl)-thiophen-3-yl-methanone. (2-Amino-phenyl)-thiophen-3-yl-methanone can be prepared by the method of Fritz Hunziker et. al.: *Europ. J. Med. Chem.* 1981, 16(5), 391.

Example 25

[4-(3,5-Dimethyl-isoxazol-4-yl)-3,4-dihydro-quinazolin-2-yl]-(R)-indan-1-yl-amine

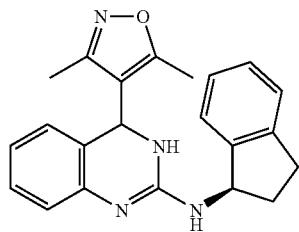

The title compound (MS: m/e=359.3 [M+H⁺]) was prepared in analogy to example 9 from (R)-1-aminoindan and (2-amino-phenyl)-(3,5-dimethyl-isoxazol-4-yl)-methanone. (2-Amino-phenyl)-(3,5-dimethyl-isoxazol-4-yl)-methanone can be prepared by the method of Leo H. Sternbach et. al.: *J. Heterocyclic Chem.* 1975, 12(1), 49.

Example 26

[4-(3,5-Dimethyl-isoxazol-4-yl)-3,4-dihydro-quinazolin-2-yl]-(S)-indan-1-yl-amine

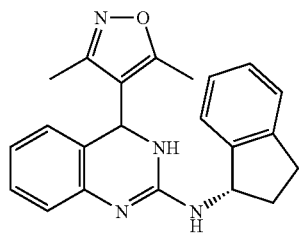

The title compound (MS: m/e=359.0 [M+H⁺]) was prepared in analogy to example 9 from (S)-1-aminoindan and (2-amino-phenyl)-(3,5-dimethyl-isoxazol-4-yl)-methanone. (2-Amino-phenyl)-(3,5-dimethyl-isoxazol-4-yl)-methanone can be prepared by the method of Leo H. Sternbach et. al.: *J. Heterocyclic Chem.* 1975, 12(1), 49.

The invention claimed is:

1. A compound of formula I

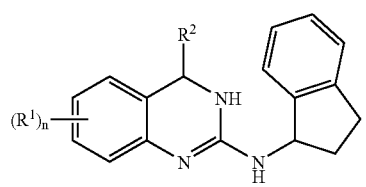

wherein
$R^1$ is hydrogen, lower alkyl, lower alkoxy, halogen or lower alkyl substituted by halogen;
$R^2$ is hydrogen, lower alkyl, aryl which is optionally substituted by one or more substituents selected from the group consisting of lower alkyl and halogen, or is thiophenyl or isoxazole; and
n is 1 or 2;
or a pharmaceutically acceptable acid addition salt thereof.

2. The compound of claim 1, wherein $R^2$ is hydrogen.

3. The compound of claim 2, selected from the group consisting of
(3,4-dihydro-quinazolin-2-yl)-(R)-indan-1-yl-amine;
(5-chloro-3,4-dihydro-quinazolin-2-yl)-indan-1-yl-amine;
indan-1-yl-(8-methyl-3,4-dihydro-quinazolin-2-yl)-amine;
(6-fluoro-3,4-dihydro-quinazolin-2-yl)-indan-1-yl-amine;
(5,6-dichloro-3,4-dihydro-quinazolin-2-yl)-indan-1-yl-amine;
(5-fluoro-3,4-dihydro-quinazolin-2-yl)-indan-1-yl-amine;
indan-1-yl-(6-methyl-3,4-dihydro-quinazolin-2-yl)-amine; and
indan-1-yl-(5-methyl-3,4-dihydro-quinazolin-2-yl)-amine.

4. The compound of claim 2, selected from the group consisting of
indan-1-yl-(6-methoxy-3,4-dihydro-quinazolin-2-yl)-amine;
(7-chloro-3,4-dihydro-quinazolin-2-yl)-indan-1-yl-amine;
indan-1-yl-(7-trifluoromethyl-3,4-dihydro-quinazolin-2-yl)-amine;
indan-1-yl-(7-methoxy-3,4-dihydro-quinazolin-2-yl)-amine;
(6,7-dimethoxy-3,4-dihydro-quinazolin-2-yl)-indan-1-yl-amine;
(3,4-dihydro-quinazolin-2-yl)-(S)-indan-1-yl-amine; and
(6-chloro-4-phenyl-3,4-dihydro-quinazolin-2-yl)-indan-1-yl-amine.

5. The compound of claim 1, wherein $R^2$ is alkyl.

6. The compound of claim 5, wherein $R^2$ is methyl.

7. The compound of claim 6, selected from the group consisting of
indan-1-yl-(4-methyl-3,4-dihydro-quinazolin-2-yl)-amine and
(6,7-dichloro-4-methyl-3,4-dihydro-quinazolin-2-yl)-indan-1-yl-amine.

8. The compound of claim 1, wherein $R^2$ is aryl, optionally substituted by one or more substituents selected from the group consisting of lower alkyl and halogen.

9. The compound of claim 8, wherein $R^2$ is phenyl, optionally substituted by halogen.

10. The compound of claim 9, selected from the group consisting of
indan-1-yl-(4-phenyl-3,4-dihydro-quinazolin-2-yl)-amine;
[4-(2,5-dichloro-phenyl)-3,4-dihydro-quinazolin-2-yl]-(S)-indan-1-yl-amine;
[4-(2,5-dichloro-phenyl)-3,4-dihydro-quinazolin-2-yl]-(R)-indan-1-yl-amine;
[6-chloro-4-(2-chloro-phenyl)-3,4-dihydro-quinazolin-2-yl]-(S)-indan-1-yl-amine; and
[6-chloro-4-(2-chloro-phenyl)-3,4-dihydro-quinazolin-2-yl]-(R)-indan-1-yl-amine.

11. The compound of claim 1, wherein $R^2$ is thiophenyl or isoxazolyl, optionally substituted by lower alkyl.

12. The compound of claim 11, selected from the group consisting of (R)-indan-1-yl-(4-thiophen-3-yl-3,4-dihydro-quinazolin-2-yl)-amine;

(S)-indan-1-yl-(4-thiophen-3-yl-3,4-dihydro-quinazolin-2-yl)-amine;

[4-(3,5-dimethyl-isoxazol-4-yl)-3,4-dihydro-quinazolin-2-yl]-(R)-indan-1-yl-amine; and

[4-(3,5-dimethyl-isoxazol-4-yl)-3,4-dihydro-quinazolin-2-yl]-(S)-indan-1-yl-amine.

13. The compound of claim 1, wherein $R^1$ is hydrogen.

14. The compound of claim 1, wherein $R^1$ is lower alkyl.

15. The compound of claim 1, wherein $R^1$ is lower alkoxy.

16. The compound of claim 1, wherein $R^1$ is halogen.

17. The compound of claim 1, wherein $R^1$ is lower alkyl substituted by halogen.

18. A process for preparing a compound of formula I

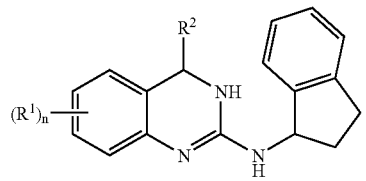

wherein $R^1$ is hydrogen, lower alkyl, lower alkoxy, halogen or lower alkyl substituted by halogen;

$R^2$ is hydrogen, lower alkyl, aryl which is optionally substituted by one or more substituents selected from the group consisting of lower alkyl and halogen, or is thiophenyl or isoxazole; and n is 1 or 2;

or a pharmaceutically acceptable acid addition salt thereof which process comprises reacting a compound of formula

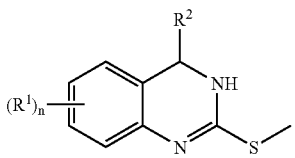

with 1-aminoindane
to obtain a compound of formula

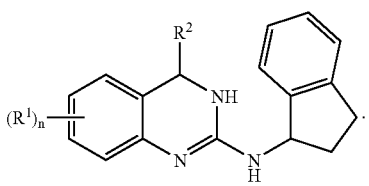

19. A pharmaceutical composition comprising a compound of formula I

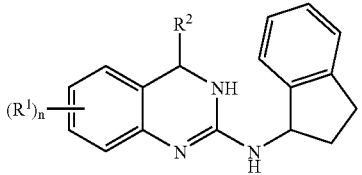

wherein $R^1$ is hydrogen, lower alkyl, lower alkoxy, halogen or lower alkyl substituted by halogen;

$R^2$ is hydrogen, lower alkyl, aryl which is optionally substituted by one or more substituents selected from the group consisting of lower alkyl and halogen, or is thiophenyl or isoxazole; and n is 1 or 2;

or a pharmaceutically acceptable acid addition salt thereof.

* * * * *

UNITED STATES PATENT AND TRADEMARK OFFICE
CERTIFICATE OF CORRECTION

PATENT NO.       : 7,348,332 B2                                     Page 1 of 1
APPLICATION NO.  : 11/399790
DATED            : March 25, 2008
INVENTOR(S)      : Alanine et al.

It is certified that error appears in the above-identified patent and that said Letters Patent is hereby corrected as shown below:

ON TITLE PAGE ITEM (75):

The inventor information for Luca Claudio Gobbi should read -- Luca Claudio Gobbi, Oberwil (CH) --.

Signed and Sealed this

Eighth Day of July, 2008

JON W. DUDAS
*Director of the United States Patent and Trademark Office*